(12) United States Patent
Vinten-Johansen

(10) Patent No.: US 7,686,781 B2
(45) Date of Patent: Mar. 30, 2010

(54) CATHETER FOR MODIFIED PERFUSION

(75) Inventor: Jakob Vinten-Johansen, Grayson, GA (US)

(73) Assignee: Emory University, Atlanta, GA (US)

( * ) Notice: Subject to any disclaimer, the term of this patent is extended or adjusted under 35 U.S.C. 154(b) by 1571 days.

(21) Appl. No.: 10/493,779

(22) PCT Filed: Oct. 25, 2002

(86) PCT No.: PCT/US02/34158

§ 371 (c)(1),
(2), (4) Date: Jun. 4, 2004

(87) PCT Pub. No.: WO03/035142

PCT Pub. Date: May 1, 2003

(65) Prior Publication Data

US 2004/0243057 A1      Dec. 2, 2004

Related U.S. Application Data

(60) Provisional application No. 60/351,203, filed on Oct. 25, 2001.

(51) Int. Cl.
*A61N 1/08* (2006.01)
(52) U.S. Cl. .............. 604/65; 604/66; 604/67; 604/96.01
(58) Field of Classification Search ......... 604/507–510, 604/4.01, 96.01, 65–67
See application file for complete search history.

(56) References Cited

U.S. PATENT DOCUMENTS 4,691,708 A * 9/1987 Kane .......................... 600/480

(Continued)

FOREIGN PATENT DOCUMENTS

WO    WO 99/04849    2/1999

(Continued)

OTHER PUBLICATIONS

Agnelli, et al., "Effects of Hirudin and Heparin on the Binding of New Fibrin to the Thrombus in t-PA Treated Rabbits," *Thromb. Haemost.*, 1991; 66(5): 592-597.

(Continued)

*Primary Examiner*—Nicholas D Lucchesi
*Assistant Examiner*—Laura A Bouchelle
(74) *Attorney, Agent, or Firm*—Ballard Spahr LLP

(57) ABSTRACT

A catheter adapted for use in passing fluids and medicines therethrough for use in the perfusion or reperfusion of blood or blood-fluid mixtures into the arteries, veins, tissues, conduits, or organs of a patient is disclosed. The catheter has an elongate tubular body with an elongate central lumen defined therein. The catheter also includes at least one occlusive balloon disposed on the exterior of and about the tubular body, and a drug delivery lumen defined within the tubular body separately of the central lumen and extending in the lengthwise direction of the tubular body. A drug delivery outlet is defined at and in communication with a distal end of the drug delivery lumen for permitting the delivery of fluids passed through the drug delivery lumen separate of any fluids passed through the central lumen of the catheter. A separate drug infusion port, in fluid communication with the drug delivery lumen, is provided at a proximal end of the catheter so that any desired fluids and/or medicines may be passed into the patient through the drug delivery lumen separately of the central lumen. The catheter may also include a pressure sensor at the distal end of the tubular body for measuring the pressure of fluid thereat during catheterization and/or fluid delivery therethrough.

15 Claims, 5 Drawing Sheets

U.S. PATENT DOCUMENTS

| | | | |
|---|---|---|---|
| 4,769,010 A | 9/1988 | Fenton, Jr. et al. | 604/180 |
| 4,781,677 A | 11/1988 | Wilcox | |
| 4,901,731 A | 2/1990 | Millar | 128/675 |
| 4,929,236 A | 5/1990 | Sampson | 604/175 |
| 4,943,277 A | 7/1990 | Bolling | 604/96 |
| 5,011,469 A | 4/1991 | Buckberg et al. | |
| 5,112,301 A | 5/1992 | Fenton, Jr. et al. | 604/30 |
| 5,129,891 A | 7/1992 | Young | 604/238 |
| 5,156,600 A | 10/1992 | Young | 604/247 |
| 5,178,612 A | 1/1993 | Fenton, Jr. | 604/283 |
| 5,190,520 A | 3/1993 | Fenton, Jr. et al. | 604/43 |
| 5,195,942 A | 3/1993 | Weil et al. | |
| 5,224,938 A | 7/1993 | Fenton, Jr. | 604/247 |
| 5,286,259 A | 2/1994 | Ganguly et al. | 604/96 |
| 5,312,337 A | 5/1994 | Flaherty et al. | 604/93 |
| 5,573,502 A | 11/1996 | LeCocq et al. | |
| 5,695,457 A | 12/1997 | St. Goar et al. | |
| 5,702,368 A | 12/1997 | Stevens et al. | |
| 5,702,880 A | 12/1997 | Segall et al. | |
| 5,755,687 A | 5/1998 | Donlon | 604/53 |
| 5,769,812 A | 6/1998 | Stevens et al. | |
| 5,792,094 A | 8/1998 | Stevens et al. | |
| 5,800,374 A | 9/1998 | Beyersdorf | |
| 5,868,776 A | 2/1999 | Wright | 606/194 |
| 5,879,499 A * | 3/1999 | Corvi | 156/175 |
| 5,935,103 A | 8/1999 | Hill | |
| 5,968,978 A | 10/1999 | Kleemann et al. | |
| 5,971,973 A | 10/1999 | Peters | |
| 5,993,382 A | 11/1999 | Pruitt, Sr. | 600/182 |
| 6,248,087 B1 | 6/2001 | Spears et al. | |
| 6,283,127 B1 | 9/2001 | Sterman et al. | |
| 6,293,920 B1 | 9/2001 | Sweezer et al. | |
| 6,306,113 B1 | 10/2001 | Beyersdorf | |
| 6,315,768 B1 * | 11/2001 | Wallace | 604/507 |
| 6,398,752 B1 | 6/2002 | Sweezer, Jr. et al. | |
| 6,423,705 B1 | 7/2002 | Tracey et al. | |
| 6,435,189 B1 | 8/2002 | Lewis et al. | |
| 6,443,922 B1 | 9/2002 | Roberts et al. | |
| RE38,081 E | 4/2003 | Faithfull et al. | |
| 6,555,059 B1 | 4/2003 | Myrick et al. | |
| 6,565,807 B1 | 5/2003 | Patterson et al. | |
| 6,576,191 B1 | 6/2003 | Myrick et al. | |
| 6,602,467 B1 | 8/2003 | Divino, Jr. et al. | |
| 6,602,468 B2 | 8/2003 | Patterson et al. | |
| 6,607,698 B1 | 8/2003 | Spears et al. | |
| 6,736,790 B2 | 5/2004 | Barbut et al. | |
| 6,746,417 B2 | 6/2004 | Spears et al. | |
| 6,899,704 B2 | 5/2005 | Sterman et al. | |
| 6,913,601 B2 | 7/2005 | St. Goar et al. | |
| 6,974,434 B2 | 12/2005 | Roberts et al. | |
| 2001/0001111 A1 | 5/2001 | Spears et al. | |
| 2001/0023334 A1 | 9/2001 | St. Goar et al. | |
| 2001/0053790 A1 | 12/2001 | Mangat et al. | |
| 2002/0013569 A1 | 1/2002 | Sterman et al. | |
| 2002/0055468 A1 | 5/2002 | Oeltgen et al. | |
| 2002/0095044 A1 | 7/2002 | Jagtap et al. | |
| 2002/0122796 A1 | 9/2002 | Cummings et al. | |
| 2003/0040531 A1 | 2/2003 | Fujishima et al. | |
| 2003/0109433 A1 | 6/2003 | Oeltgen et al. | |
| 2003/0113744 A1 | 6/2003 | O'Toole et al. | |
| 2003/0118578 A1 | 6/2003 | Rosenzweig et al. | |
| 2003/0145865 A1 | 8/2003 | Sterman et al. | |
| 2003/0149050 A1 | 8/2003 | Jagtap et al. | |
| 2003/0158247 A1 | 8/2003 | Linz et al. | |
| 2003/0211998 A1 | 11/2003 | Oeltgen et al. | |
| 2003/0216582 A1 | 11/2003 | Nikolaides et al. | |
| 2003/0220383 A1 | 11/2003 | Lang et al. | |
| 2004/0111079 A1 | 6/2004 | Hayes et al. | |
| 2004/0131607 A1 | 7/2004 | Carroll et al. | |
| 2004/0138608 A1 | 7/2004 | Barbut et al. | |
| 2004/0138728 A1 | 7/2004 | Wong et al. | |
| 2004/0255956 A1 | 12/2004 | Vinten-Johansen et al. | |
| 2005/0037995 A1 | 2/2005 | Lockwood et al. | |
| 2005/0065097 A1 | 3/2005 | Lockwood et al. | |
| 2005/0096715 A1 | 5/2005 | Magers | |
| 2005/0143475 A1 | 6/2005 | Lockwood et al. | |
| 2005/0187221 A1 | 8/2005 | Matsuda et al. | |
| 2005/0203065 A1 | 9/2005 | Smits et al. | |
| 2005/0214295 A1 | 9/2005 | Paul et al. | |
| 2005/0215533 A1 | 9/2005 | Gottlieb et al. | |
| 2005/0222038 A1 | 10/2005 | Oeltgen et al. | |
| 2005/0230313 A1 | 10/2005 | O'Mahony et al. | |
| 2006/0029589 A1 | 2/2006 | Weiler | |
| 2006/0034801 A1 | 2/2006 | Jalkanen | |
| 2006/0051407 A1 | 3/2006 | Richter et al. | |
| 2006/0067925 A1 | 3/2006 | Labhasetwar et al. | |
| 2006/0095104 A1 | 5/2006 | Magers et al. | |
| 2006/0100639 A1 | 5/2006 | Levin et al. | |
| 2006/0111421 A1 | 5/2006 | Chadwick et al. | |
| 2006/0124141 A1 | 6/2006 | Dobak, III | |
| 2006/0136023 A1 | 6/2006 | Dobak, III | |
| 2006/0140939 A1 | 6/2006 | Fung | |
| 2006/0276743 A1 | 12/2006 | MacMahon et al. | |

FOREIGN PATENT DOCUMENTS

| | | |
|---|---|---|
| WO | WO 03/035142 | 5/2003 |
| WO | WO 03/059266 | 7/2003 |
| WO | WO 2006/069170 | 6/2006 |
| WO | WO 2008/115603 | 9/2008 |

OTHER PUBLICATIONS

Ambrosio, et al., "Improvement of postischemic myocardial function and metabolism induced by administration of deferoxamine at the time of reflow: the role of iron in the pathogenesis of reperfusion injury," *Circulation*, 1987; 76(4): 906-915.

Auchampach, et al., "Anti-ischaemic actions of potassium channel openers in experimental myocardial ischaemia/reperfusion injury in dogs," *Eur. Heart Jour.*, 1993; 14(Supp. B): 10-15.

Auchampach, et al., "Reduction in Myocardial Infarct Size by the New Potassium Channel Opener Bimakalim," *J. Cardiovasc. Pharmacol.*, 1994; 23(4): 554-561.

Auchampach, et al., "Pharmacological Evidence for a Role of ATP-Dependent Potassium Channels in Myocardial Stunning," *Circulation*, 1992; 86: 311-319.

Axford-Gately, et al., "Myocardial infarct size reduction by single high dose or repeated low dose vitamin E supplementation in rabbits," *Can. J. Cardiol.*, 1993; 9(1): 94-98.

Baines, et al., "Protein Tyrosine Kinase is Downstream of Protein Kinase C for Ischemic Preconditioning's Anti-Infarct Effect in the Rabbit Heart," *J. Mol. Cell Cardiol.*, 1998; 30: 383-392.

Balakirev, et al., "Gradual Changes in Permeability of Inner Mitochondrial Membrane Precede the Mitochondrial Permeability Transition," *Arch. Biochem. Biophys.*, 1998; 356(1): 46-54.

Barta, et al., "Protective Effect of Alpha-tocopherol and L-Ascorbic Acid against the Ischemic-Reperfusion Injury in Patients During Open-heart Surgery," *Bratisl. Lek. Listy*, 1991; 92(3-4): 174-183.

Buus, et al., "Influence of Nitric Oxide Synthase and Adrenergic Inhibition on Adenosine-Induced Myocardial Hyperemia," *Circulation*, 2001; 104(19): 2305-2310.

Chen, et al., "Prostacyclin Analogue (OP-2507) Attenuates Hepatic Microcirculatory Derangement, Energy Depletion, and Lipid Peroxidation in a Rat Model of Reperfusion Injury," *J. Surg. Res.*, 1998; 80(2): 333-338.

Chiari, et al., "Isoflurane Protects against Myocardial Infarction during Early Reperfusion by Activation of Phosphatidylinositol-3-Kinase Signal Transduction: Evidence for Anesthetic-induced Postconditioning in Rabbits," *Anesthesiology*, 2005;102(1): 102-109.

Chiari, et al., "Role of Endothelial Nitric Oxide Synthase as a Trigger and Mediator of Isoflurane-induced Delayed Preconditioning in Rabbit Myocardium," *Anesthesiology*, 2005; 103(1): 74-83.

Davenpeck, et al., "Inhibition of Endothelial-Derived Nitric Oxide Promotes P-Selectin Expression and Actions in the Rat Microcirculation," *Gastroenterology*, 1994; 107: 1050-1058.

Downey, J., "Ischemic Preconditioning: Nature's Own Cardioprotective Intervention," *Trends Cardiovasc. Med.*, 1992; 2: 170-176.

Duilio, et al., "Neutrophils are primary source of $O_2$ radicals during reperfusion after prolonged myocardial ischemia," *Am. J. Physiol. Heart Circ. Physiol.*, 2001; 280: H2649-H2657.

Euler, D., "Role of oxygen-derived free radicals in canine reperfusion arrhythmias," *Am. J. Physiol. Heart Circ. Physiol.*, 1995; 268: H295-H300.

Garcia-Dorado, et al., "Bringing preconditioning and postconditioning into focus." *Cardiovasc. Res.*, 2006; 70: 167-169.

Griffiths, et al., "Protection by Cyclosporin A of Ischemia/Reperfusion-Induced Damage in Isolated Rat Hearts," *J. Mol. Cell Cardiol.*, 1993; 25: 1461-1469.

Gross, et al., "Cardioprotective Effects of Nicorandil." *J. Cardiovasc. Pharmacol.*, 1992; 20 (Suppl 3): S22-S28.

Gross, et al., "The ATP-Regulated Potassium Channel in Ischemia-Reperfusion Injury," *Ann. N.Y. Acad. Sci.*, 1994; 723: 71-81.

Grover, et al., "The Protective Effects of Cromakalim and Pinacidil on Reperfusion Function and Infarct Size in Isolated Perfused Rat Hearts and Anesthetized Dogs," *Cardiovasc. Drugs Ther.*, 1990; 4: 465-474.

Gumina, et al., "A New Sodium/Hydrogen Exchange Inhibitor, EMD 85131, Limits Infarct Size in Dogs When Administered Before or After Coronary Artery Occlusion," *J. Pharmacol. Exp. Ther.*, 1998; 286(1): 175-183.

Gunnes, et al., "Improved energy preservation following gentle reperfusion after hypothermic, ischemic cardioplegia in infarcted rat hearts." *Eur. J. of Cardiothorac. Surg.*, 1987; 1: 139-143.

Halkos, et al., "Myocardial Protection With Postconditioning is Not Enhanced by Ischemic Preconditioning," *Ann. Thorac. Surg.*, 2004; 78(3):961-969.

Hausenloy, et al., "Ischemic preconditioning protects by activating prosurvival kinases at reperfusion," *Am. J. Physiol. Heart Circ. Physiol.*, 2005; 288: H971-H976.

Hausenloy, et al., "New directions for protecting the heart against ischaemia-reperfusion injury: targeting the Reperfusion Injury Salvage Kinase (RISK)-pathway," *Cardiovasc. Res.*, 2004; 61(3): 448-460.

Hausenloy, et al., "Inhibiting mitochondrial permeability transition pore opening: a new paradigm for myocardial preconditioning?" *Cardiovasc. Res.*, 2002; 55: 534-543.

Hirano, et al., "The combined use of prostaglandin $I_2$ analogue (OP-2507) and thromboxane $A_2$ synthetase inhibitor (OKY-046) strongly inhibits atherosclerosis of aortic allografts in rats," *Surgery*, 2001; 129(5): 595-605.

Hoshida, et al., "Nitric Oxide Synthase Protects the Heart against Ischemia-Reperfusion Injury in Rabbits," *J. Pharmacol. Exp. Ther.*, 1995; 274(1): 413-418.

Jackson, et al., "Prostacyclin-induced vasodilation in rabbit heart is mediated by ATP-sensitive potassium channels," *Am. J. Physiol.*, 1993; 264: H238-H243.

Jiang, et al., "Postconditioning Reduces Reperfusion Injury by Inhibiting the Tissue Factor-Thrombin Pathway in a Closed-Chest Porcine Model Of Ischemia-Reperfusion," *Scientific Sessions*, 2005; Abstract No. 1554.

Jiang, et al., "Which 'survival' and/or 'death' kinases contribute to postconditioning in rabbit heart?," *Journal of Molecular And Cellular Cardiology*, 2005; 38: 809-885, Abstract No. 129.

Jordan, et al., "The role of neutrophils in myocardial ischemia-reperfusion injury." *Cardiovas. Res.*, 1999; 43: 860-878.

Karmazyn, M., "Pharmacology and clinical assessment of cariporide for the treatment coronary artery diseases," *Exp. Opin. Invest. Drugs*, 2000; 9(5): 1099-1108.

Kato, K., "Haemodynamic and clinical effects of an intravenous potassium channel opener—a review," *Eur. Heart Jour.*, 1993; 14 (Supp. B): 40-47.

Katoh, et al., "Deferoxamine Reduces the Reperfusion Injury in Isolated Neonatal Rabbit Hearts After Hypothermic Preservation," *Surg. Today, Jpn. J. Surg.*, 1993; 23: 424-429.

Kerendi, et al., "Remote postconditioning," *Basic Res. in Cardiol.*, 2005; 100: 404-412.

Kin, et al., "Pharmacological Enhancement of Post-Conditioning (PEP-C) Increases Myocardial Salvage after Acute Myocardial Infarction," *Scientific Sessions*, 2005; Abstract No. 1556.

Kin, et al., "Neutrophil depletion and oxidant inhibition reduce myocardial apoptosis by inhibiting activation of caspase-3 and up-regulating bcl-2 expression," *Journal of Molecular and Cellular Cardiology*, 2005; 38: 809-885, Abstract No. 48.

Kin, et al., "Activation of opioid receptors mediates the infarct size reduction by Postconditioning," *Journal of Molecular and Cellular Cardiology*, 2005; 38: 809-885, Abstract No. 49.

Kin, et al., "Postconditioning attenuates myocardial ischemia-reperfusion injury by inhibiting events in the early minutes of reperfusion," *Cardiovasc. Res.*, 2004; 62: 74-85.

Kin, et al., "Postconditioning reduces infarct size via adenosine receptor activation by endogenous adenosine," *Cardiovascular Res.*, 2005; 67: 124-133.

Kodani, et al., "Protection of IB-MECA against myocardial stunning in conscious rabbits is not mediated by the $A_1$ adenosine receptor," *Basic Res. Cardiol.*, 2001; 96(5): 487-496.

Lam, et al., "The Effect of Aurintricarboxylic Acid, an Endonuclease Inhibitor, on Ischemia/Reperfusion Damage in Rat Retina," *Jour. Ocular Pharmacol. Therap.*, 1995; 11(3): 253-259.

Lefer, et al., "Endothelial Dysfunction and Neutrophil Adherence as Critical Events in the Development of Reperfusion Injury," *Agents Actions (Suppl)*, 1993; 41: 127-135.

Linz, et al., "Dose-Dependent Reduction Of Myocardial Infarct Mass In Rabbits by the NHE-1 Inhibitor Cariporide (HOE 642)," *Clin. Exp. Hypertens.*, 1998; 20(7): 733-749.

Miura, et al., "Mitochondrial ATP-Sensitive $K^+$ Channels Play a Role in Cardioprotection by $Na^+$- $H^+$ Exchange Inhibition Against Ischemia/Reperfusion Injury," *J. Am. Coll. Cardiol.*, 2001; 37(3): 957-963.

Mizumura, et al., "Bimakalim, an ATP-Sensitive Potassium Channel Opener, Mimics the Effects of Ischemic Preconditioning to Reduce Infarct Size, Adenosine Release, and Neutrophil Function in Dogs," *Circulation*, 1995; 92: 1236-1245.

Murry, et al., "Editorial Comment: New Insights Into Potential Mechanisms of Ischemic Preconditioning," *Circulation*, 1991; 84: 442-445.

Murry, et al., "Ischemic Preconditioning Slows Energy Metabolism and Delays Ultrastructural Damage During a Sustained Ischemic Episode," *Circ. Res.*, 1990; 66: 913-931.

Murry, et al., "Preconditioning with ischemia: a delay of lethal cell injury in ischemic myocardium," *Circulation*, 1986; 74(5): 1124-1136.

Mykytenko, et al., "Long-term inhibition of myocardial infarction by postconditioning during reperfusion," *Basic Res. Cardiol.*, 2007; 102(1): 90-100.

Neely, et al., "$A_1$ adenosine receptor antagonists block ischemia-reperfusion injury of the lung," *Amer. J. Physiol.*, 1995; 268(6): L1036-L1046.

Neely, et al., "$A_1$ Adenosine Receptor Antagonists Block Ischemia-Reperfusion Injury of the Heart," *Circulation*, 1996; 94(9 Suppl.): II376-II380.

Ockaili, et al., "Sildenafil (Viagra) induces powerful cardioprotective effect via opening of mitochondrial $K_{ATP}$ channels in rabbits," *Am. J. Physiol. Heart Circ. Physiol.*, 2002; 283: H1263-H1269.

Okamoto, et al., "Perivascular Inflammation After Balloon Angioplasty of Porcine Coronary Arteries," *Circulation*, 2001; 104: 2228-2235.

Ooiwa, et al., "Examination of Two Small-Molecule Antiperoxidative Agents in a Rabbit Model of Postischemic Myocardial Infarction," *J. Cardiovasc. Pharmacol.*, 1991; 17(5): 761-767.

Piper, et al., "A fresh look at reperfusion injury," *Cardiovasc. Res.*, 1998; 38: 291-300.

Piper, et al., "Cellular Mechanisms of Ischemia-Reperfusion Injury." *Ann. Thorac. Surg.*, 2003; 75: S644-S648.

Piper, et al., "The first minutes of reperfusion: a window of opportunity for cardioprotection," *Cardiovasc. Res.*, 2004; 61(3): 365-371.

Piper, et al., "Prime Causes of Rapid Cardiomyocyte Death During Reperfusion," *Ann. Thorac. Surg.*, 1999; 68: 1913-1919.

Qin, et al., "Acetylcholine but Not Adenosine Triggers Preconditioning by a Pathway Involving Src and P13 Kinases," *Circulation, Suppl. II*, 2002; 106(19), Abstract No. 1573.

Reimer, et al., "Four brief periods of myocardial ischemia cause no cumulative ATP loss or necrosis," *Am. J. Physiol.*, 1986; 251: H1306-H1315.

Reimer, et al., "The 'Wavefront Phenomenon' of Ischemic Cell Death—1. Myocardial Infarct Size vs Duration of Coronary Occlusion in Dogs," *Circulation*, 1977; 56(5): 786-794.

Reimer, et al., "The 'Wavefront Phenomenon' of Myocardial Ischemic Cell Death—II. Transmural Progression of Necrosis within the Framework of Ischemic Bed Size (Myocardium at Risk) and Collateral Flow," *Lab Invest.*, 1979; 40(6): 633-644.

Rosenbaum, et al., "Pretreatment with Intraventricular Aurintricarboxylic Acid Decreases Infarct Size by Inhibiting Apoptosis following Transient Global Ischemia in Gerbils," *Ann. Neurol.*, 1998; 43(5): 654-660.

Sanz et al., "Dissociation between anti-infarct effect and anti-edema effect of ischemic preconditioning," *Am. J. Physiol.*, 2003; 268 (1 Pt 2): H233-41, (Abstract).

Sato, et al., "Gradual Reperfusion Reduces Infarct Size and Endothelial Injury but Augments Neutrophil Accumulation." *Ann. Thorac. Surg.*, 1997; 64: 1099-1107.

Schipke, et al., "Postkonditionierung: Ein kurzer Überblick," *Herz*, 2006; 31(6): 600-606.

Schultz, et al., "Opioids and cardioprotection," *Pharmacol. Ther.*, 2001; 89(2): 123-137.

Staat, et al., "Postconditioning the Human Heart," *Circulation*, 2005; 112: 2143-2148.

Sun, et al., "Postconditioning attenuates cardiomyocyte apoptosis via inhibition of JNK and p38 mitogen-activated protein kinase signaling pathways," *Apoptosis*, 2006; 11(9): 1583-1593.

Sun, et al., "Hypoxic postconditioning reduces cardiomyocyte loss by inhibiting ROS generation and intracellular $Ca^{2+}$ overload," *Am. J. Physiol. Heart Circ. Physiol.*, 2005; 288(4): H1900-H1908.

Thourani, et al., "Nonanticoagulant heparin inhibits NF-κB activation and attenuates myocardial reperfusion injury," *Am. J. Physiol. Heart Circ. Physiol.*, 2000; 48: H2084-H2093.

Vinten-Johansen, J., "Reperfusion Injury: Idle Curiosity or Therapeutic Vector?" *Journal of Thrombosis and Thrombolysis*, 1997; 4: 59-61.

Vinten-Johansen, J., "Involvement of neutrophils in the pathogenesis of lethal myocardial reperfusion injury," *Cardiovasc. Res.*, 2004; 61: 481-497.

Vinten-Johansen, et al., "Controlled coronary hydrodynamics at the time of reperfusion reduces postischemic injury," *Coronary Artery Disease*, 1992; 3: 1081-1093.

Vinten-Johansen, et al., "Postconditioning—A new link in nature's armor against myocardial ischemia reperfusion injury," *Basic Res. Cardiol.*, 2005; 100(4): 295-310.

Vinten-Johansen, et al., "Postconditioning—A Simple, Clinically Applicable Procedure to Improve Revascularization in Acute Myocardial Infarction," *Circulation*, 2005; 112: 2085-2088.

Vinten-Johansen, et al., "Myocardial protection in reperfusion with postconditioning," *Expert Rev. Cardiovasc. Ther.*, 2005; 3(6): 1035-1045.

Vinten-Johansen, J., "Postconditioning: a mechanical maneuver that triggers biological and molecular cardioprotective responses to reperfusion," *Heart Fail. Rev.*, 2007; 12(3-4): 235-244.

Vinten-Johansen, et al., "Preconditioning and postconditioning: innate cardioprotection from ischemia-reperfusion injury," *J. Appl. Physiol.*, 2007; 103(4): 1441-1448.

Vinten-Johansen, et al., "Post-Conditioning Reduces Myocardial Injury by Inhibiting Reactive Oxygen Species During Reperfusion," *Circulation*, 2003; 108(Suppl.): IV-219 (Abstract).

Weber, et al., "Cardioprotection by Blockade of Src Activity in Models of Acute Myocardial Infarction," *Circulation, Suppl. II*, 2002; 106(19), Abstract No. 1574.

Yang, et al., "Permanent Reduction in Myocardial Infarct Size by Postconditioning in Patients after Primary Coronary Angioplasty," *Circulation, Suppl. II*, 2006; 114(18), Abstract No. 3795.

Yang, et al., "Multiple, Brief Coronary Occlusions During Early Reperfusion Protect Rabbit Hearts by Activation of ERK and Production of Nitric Oxide," *Circulation (Suppl)*, 2003; 108(17), IV-745 (Abstract).

Zatta, et al., "Postconditioning reduces infarct size via activation of adenosine $A_{2A}$ and $A_3$ receptor subtypes," *Journal of Molecular and Cellular Cardiology*, 2005; 38: 809-885, Abstract No. 4.

Zatta, et al., "Infarct-sparing effect of myocardial postconditioning is dependent on protein kinase C signaling," *Cardiovasc. Res.*, 2006; 70(2): 315-324.

Zeymer, et al., "The $Na^+/H^+$ Exchange Inhibitor Eniporide as an Adjunct to Early Reperfusion Therapy for Acute Myocardial Infarction," *J. Am. Coll. Cardiol.*, 2001; 38(6): 1644-1650.

Zhao, et al., "Dynamic Progression of Contractile and Endothelial Dysfunction and Infarct Extension in the Late Phase of Reperfusion," *J. Surg. Res.*, 2000; 94: 133-144.

Zhao, et al., "Postconditioning: Reduction of reperfusion-induced injury," *Cardiovas. Res.*, 2006; 70: 200-211.

Zhao, et al., "Hypoxic Postconditioning Attenuates Cardiomyocyte Apoptosis via Inhibition of JNK and p38 Mitogen-Activated Protein Kinase Pathway," International Society for Heart Research, *J. Molecular & Cellullar Cardiol.*, 2005; 38: 870 (Abstract).

Zhao, et al., "Reduction in Infarct Size and Preservation of Endothelial Function by Ischemic Postconditioning: Comparison with Ischemic Preconditioning." *Circulation, Suppl. II*, 2002; 106(19), Abstract No. 1575.

Zhao et al. "Hypoxic Post-Conditioning Reduces Cardiomyocyte Loss by Inhibiting Reactive Oxygen Species-Triggered Mitochondrial Calcium Overload," *Circulation (Suppl.)*, 2003; 108(17): IV-174 (Abstract).

Zhao, et al. "Inhibition of myocardial injury by ischemic postconditioning during reperfusion: comparison with ischemic preconditioning," *Am. J. Physiol. Heart Circ. Physiol.*, 2003; 285: H579-H588.

Zhao, et al., "Progressively developed myocardial apoptotic cell death during late phase of reperfusion," *Apoptosis*, 2001; 6(4):279-290.

Zhao, et al., "Infarct Extension and Dynamic Coronary Endothelial Dysfunction in the Late Reperfusion Phase," *Circulation, Suppl. I*, 1998; Abstract No. 4169.

\* cited by examiner

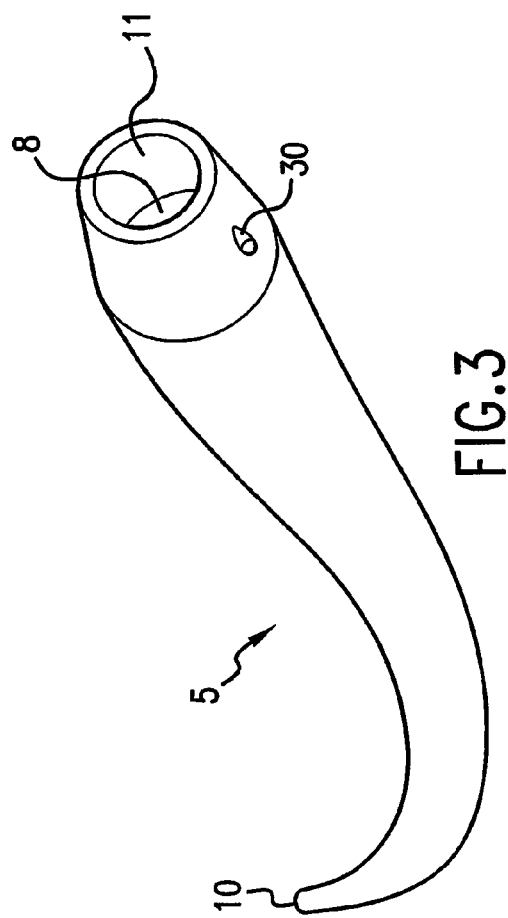
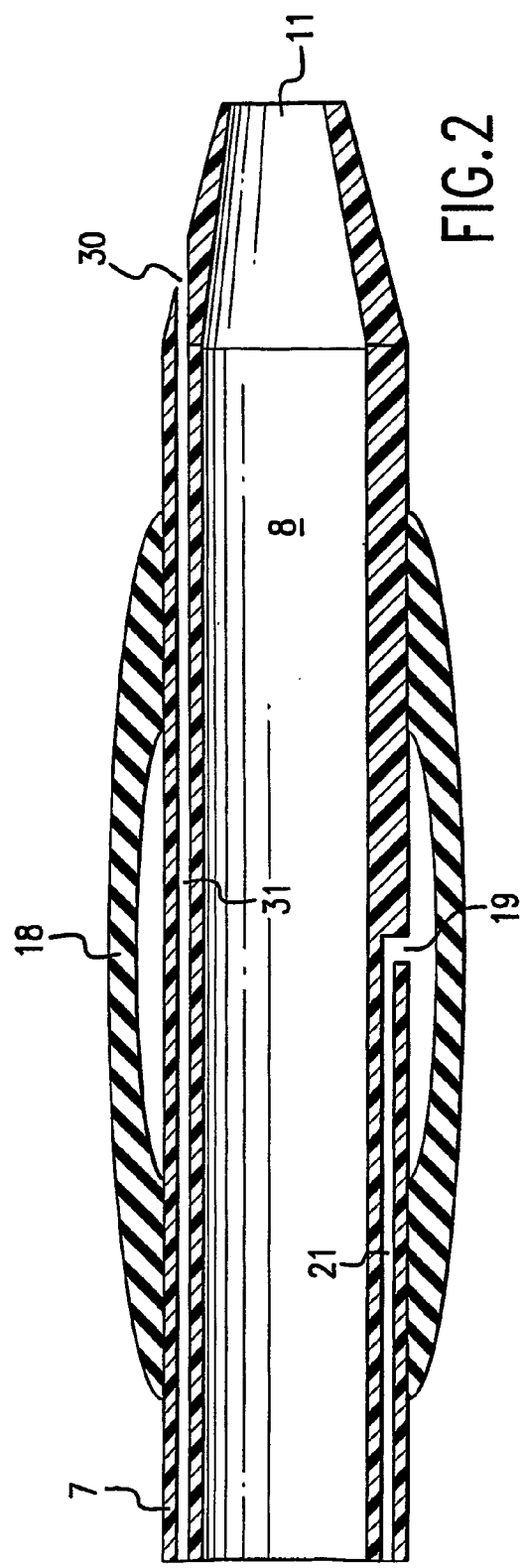

CATHETER FOR MODIFIED PERFUSION

CROSS-REFERENCE TO RELATED APPLICATION

This application claims priority to provisional U.S. Patent Application Ser. No. 60/351,203, filed on Oct. 25, 2001, in the United States Patent and Trademark Office, which application is incorporated fully herein by this reference.

FIELD OF THE INVENTION

The present invention relates in general to medical devices. More particularly, the invention relates to a catheter adapted to pass fluids, or blood in combination with fluids, therethrough for the perfusion or reperfusion of the veins, arteries, tissues, and organs of a patient.

BACKGROUND OF THE INVENTION

The construction and use of catheters and related medical devices is well known. Current technologies allow for the catheterization of arteries and veins, and allow also for the expansion of atherosclerotic plaques in an angioplasty procedure. However, these existing technologies do not allow for the delivery of drugs, especially short-acting drugs to the target area of an organ, for example the heart. In addition, the current devices which permit the delivery of drugs do not allow for the exact control of the concentration of the drug at the site of action, because the drugs are delivered systemically and because the drug delivery may tend to vary due to the flow rate and the volume of the drug(s) being passed through the catheter. Moreover, the controlled delivery of blood, fluids or a combination thereof cannot be achieved, so the control over the conditions and compositions during perfusion or reperfusion of organs and tissues cannot be exercised.

The current embodiments of catheters, as described above, allow the application of principals of modified perfusion to organs and tissues. These principals have been developed and in use over the past 10-15 years. However, the lack of a delivery technology, or in this instance, a delivery device, has impeded the clinical application of modified perfusion and reperfusion.

What is needed, therefore, is an improved catheter constructed to permit the controlled delivery of blood, or a combination of fluids, medications and blood therethrough and into the arteries, veins, organs, or tissues of a patient, and which is also suitable for use in the modified perfusion or reperfusion of the arteries, veins, organs, or tissues of a patient.

SUMMARY OF THE INVENTION

The present invention overcomes some of the design deficiencies of the known catheters by providing a catheter adapted for the controlled delivery of fluids and/or medicines therethrough and into the arteries, veins, organs, or tissues of a patient, specifically allowing delivery at known fluid pressures in the distal artery, vein or other conduit or tissue. The catheter of this invention includes an elongate tubular body defining a continuous central lumen extending through the catheter body from a proximal end to a spaced distal end thereof. A fluid-tight connector, which may for example comprise a luer-type connector, is provided at the proximal end of the tubular body and is in sealed fluid communication with the central lumen.

In use, a sheath is inserted into the access site (artery, vein or other conduit) through which the catheter is thereafter inserted. This sheath is retained in the vessel during the catheter procedure, and is provided with a port defined therein and through which the pressure in proximity to the sheath, that is the proximal pressure, may be measured. The proximal pressure measurement port may be placed into sealed fluid communication with any of the known types of fluid pressure measurement devices, as desired.

In one embodiment, an occlusive balloon is positioned to and affixed about the tubular body of the catheter, for example at the distal end thereof, and is adapted for use in known fashion. A balloon inflation port is defined within the tubular body of the catheter, and opens into the interior of the balloon. The inflation port is formed to be in sealed fluid communication with an elongate balloon inflation passageway defined within or external to the catheter body. The inflation passageway terminates at its opposite end in a balloon inlet port at the proximal end of the catheter body. The catheter may be used in conjunction with either one of a pressure wire or a flow wire, in conventional and otherwise known fashion.

In a second embodiment, a pair of spaced occlusive balloons are positioned on and about the catheter, and are adapted to be inflated or deflated together, or separately, all as desired. Separate balloon inflation ports are defined within the tubular body of the catheter, and each port opens into the interior of its respective balloon. The respective inflation ports are each formed to be in sealed fluid communication with separate and elongate balloon inflation passageways defined within, or external to, the catheter body. The inflation passageways each terminate at their opposite ends in a respective balloon inlet port at the proximal end of the catheter body.

In one embodiment, a solid state or electronic pressure sensor is affixed to the exterior of, or is otherwise embedded within, the distal end of the catheter and is adapted for measuring fluid pressure during catheterization, as well as the pressure of fluid delivery therethrough. In an alternate embodiment, a fluid filled pressure port is defined at the distal end of the catheter body and extends through a fluid filled passageway to the proximal end of the catheter body, where any known type of a fluid pressure measurement device, for example a fluid-filled transducer, adapted for use with a fluid pressure port may be used.

In yet another embodiment of the invention, the catheter is provided with an elongate drug delivery lumen defined within or external to the catheter body and separately of the central lumen. The drug delivery lumen defines a drug delivery outlet or discharge port at the distal end of the catheter in sealed fluid communication with the drug delivery lumen. The drug delivery lumen terminates at its proximal end in a drug infusion port which is also in sealed fluid communication with the drug delivery lumen. So constructed, the desired fluids may be mixed externally of and/or otherwise passed separately of the fluids within the central lumen in a controlled manner of delivery.

BRIEF DESCRIPTION OF THE DRAWINGS

FIG. 2 is a cross-sectioned view of the distal end of the catheter of FIG. 1.

FIG. 3 is a perspective view of the distal end of the catheter of FIG. 1.

DETAILED DESCRIPTION

Figure 1:
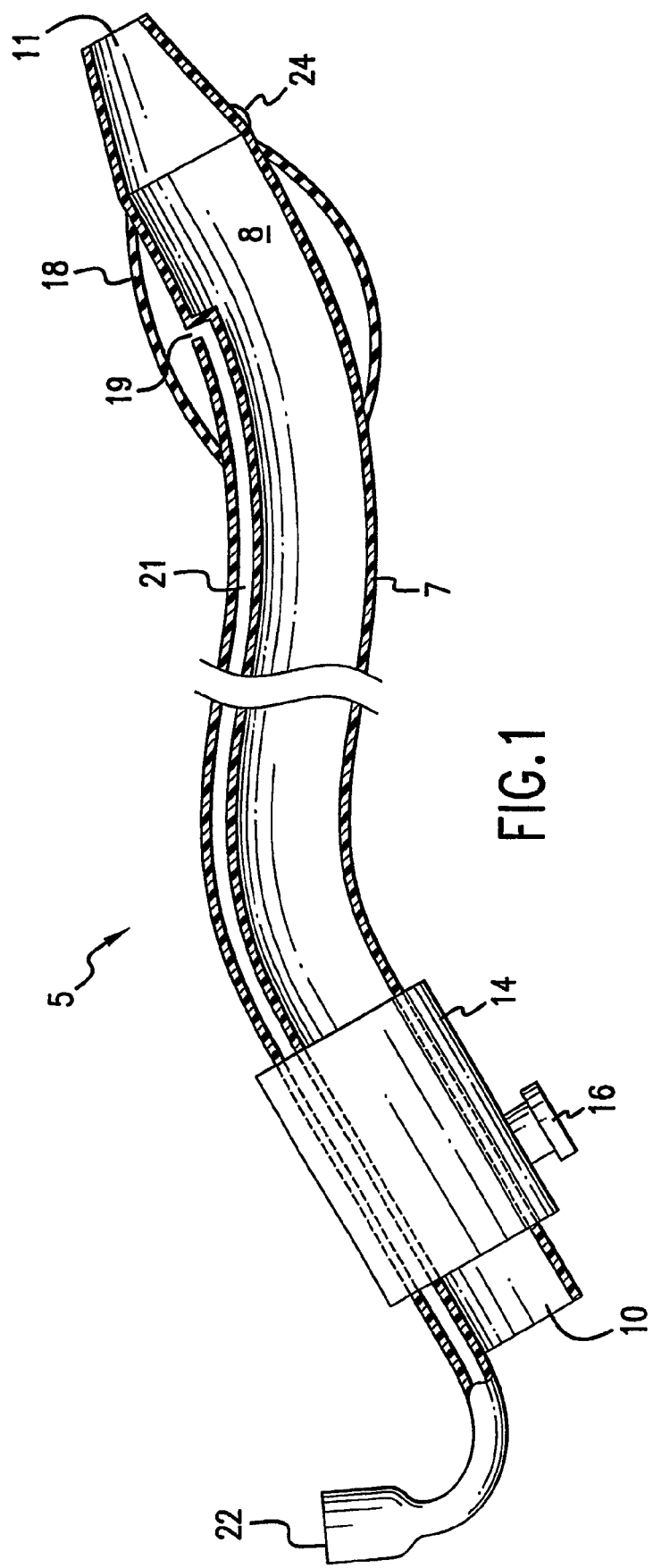
FIG. 1 is cross-sectioned view of a first embodiment of the catheter of the invention.

Referring now in detail to the drawings, in which like reference characters indicate like parts throughout the several views, a first embodiment of a catheter 5 of the invention is illustrated in FIGS. 1-4. The catheter is formed as an elongate tubular body 7 which defines a continuous central lumen 8 therein. The central lumen extends from a proximal end 10 of the catheter body to a spaced distal end 11 thereof. The central lumen 8 is preferably designed to allow for a fluid flow therethrough, either blood or a crystalloid, or a combination thereof, of approximately 100 milliliters per minute, this flow ranging from approximately one to approximately one-hundred milliliters per minute. Also, this embodiment of the catheter, as well as the other catheter embodiments discussed herein, may be used in conjunction with either one of a pressure wire or a flow wire, in conventional and otherwise known fashion.

Figure 5:
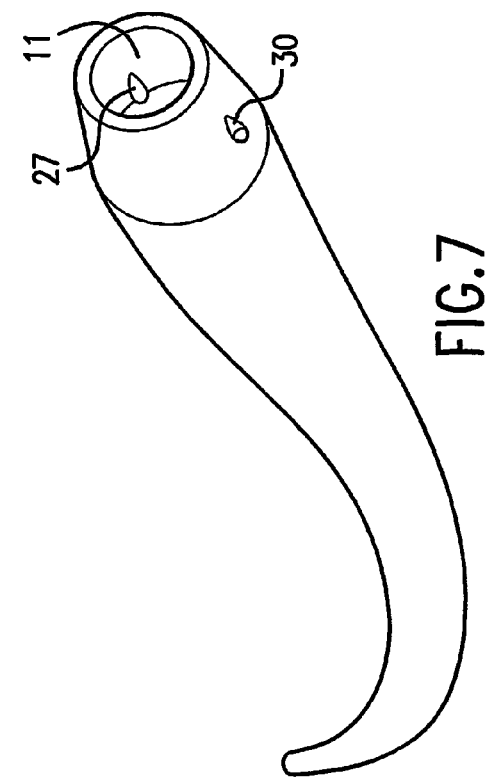
FIG. 5 is a partial and enlarged view of the proximal end of the catheters of FIGS. 1 and 4.
Figure 7:
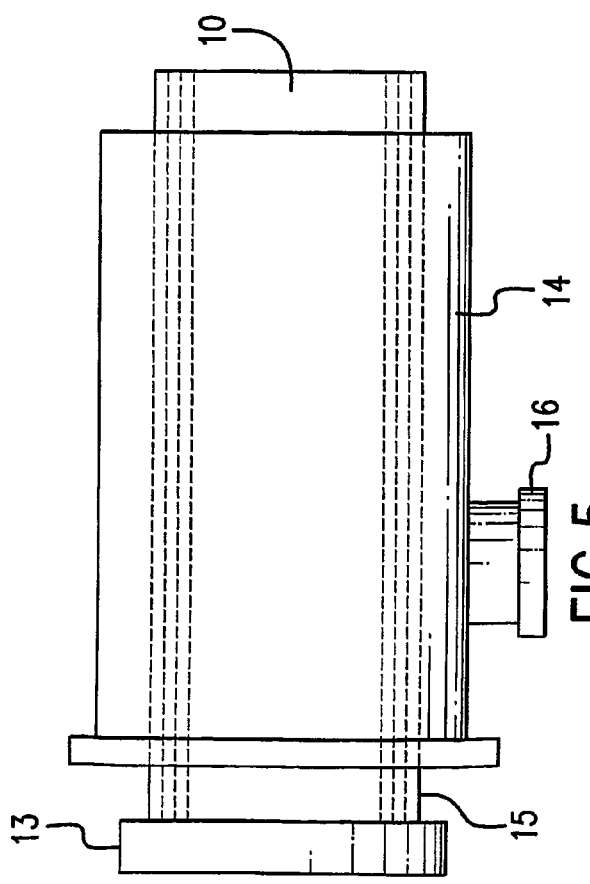
FIG. 7 is a perspective view of the distal end of the catheter of FIG. 4.

A luer-type of connector 13 (FIG. 5) is provided at the proximal end of the catheter, and which is constructed in known fashion for receiving in sealed fluid-tight communication the supply line(s) for the fluid(s) to be passed through the central lumen. The proximal end of the catheter is also provided with a proximal insertion sheath 14 extended about the exterior surface of the catheter, with a septum 15 (FIG. 5) sealing the sheath about the catheter.

The proximal insertion sheath allows the catheter to be inserted into the vessel for ultimate vascular access of the target vessel or organ. It is modified to allow measurement of vascular pressure in the vicinity of the insertion of the sheath. The sheath is similar to those currently used to insert catheters by the Seldinger technique, in which a guide wire is inserted into the access vessel from a percutaneous approach or direct cut-down, and over which a guide catheter and a stylet are inserted into an artery or vein convenient for use as an access. The stylet (not shown) is subsequently removed as the guidewire and guide catheter are advanced.

The septum 15 at the proximal end of the sheath closes to prevent the flow of blood from inside the vessel to the outside. The guidewire, followed by the perfusion catheter, is then inserted through the septum which seals around the wire and catheter to maintain hemostasis. The guidewire and catheter are then advanced toward the target vessel in known fashion, for example, as used in angioplasty or angiographic procedures. The perfusion catheter may be used in conjunction with a guide catheter for procedures performed in known fashion for angioplasty and/or other coronary catheterization procedures. In addition, the perfusion catheter may be used in conjunction with, or in lieu of an angioplasty catheter to cross the plaque site and expand the site of stenosis using the catheter balloons.

The sheath 14 includes an outlet or a pressure measurement port 16 defined therein for use in measuring the vessel blood pressure near the proximal end of the catheter in association with any of the known types of fluid pressure measurement devices (not illustrated) adapted to be received thereat. The port 16 may be fashioned as a luer-type of connector, if so desired. The pressure sheath 14 in association with the outlet port 16 may thus be used to measure and/or monitor the proximal arterial or venous blood pressure of the patient, or used as a target pressure for use in adjusting the fluid pump rates to in turn control the distal, arterial or venous fluid flow rate and pressures. In addition, the port 16 may be used as a general intravenous access for administration of fluids or drugs.

An occlusive balloon 18 of known construction is carried on and extends about the tubular body of the catheter intermediate the proximal and the distal ends, respectively, of the catheter as illustrated in FIGS. 1, 2, 4, and 6. A balloon inflation port 19 is defined within the body of the catheter in sealed fluid/air-tight communication with the balloon interior. An elongate balloon inflation passageway 21 is defined within or otherwise formed as a part of the catheter body separate of the central lumen. The passageway 21 is a hydraulic passageway in fluid communication with the balloon inflation port, and extends to a balloon inlet port 22 situated at the proximal end of the catheter (FIG. 1), to which a known type of balloon inflation device (not illustrated) may be attached.

Figure 4:
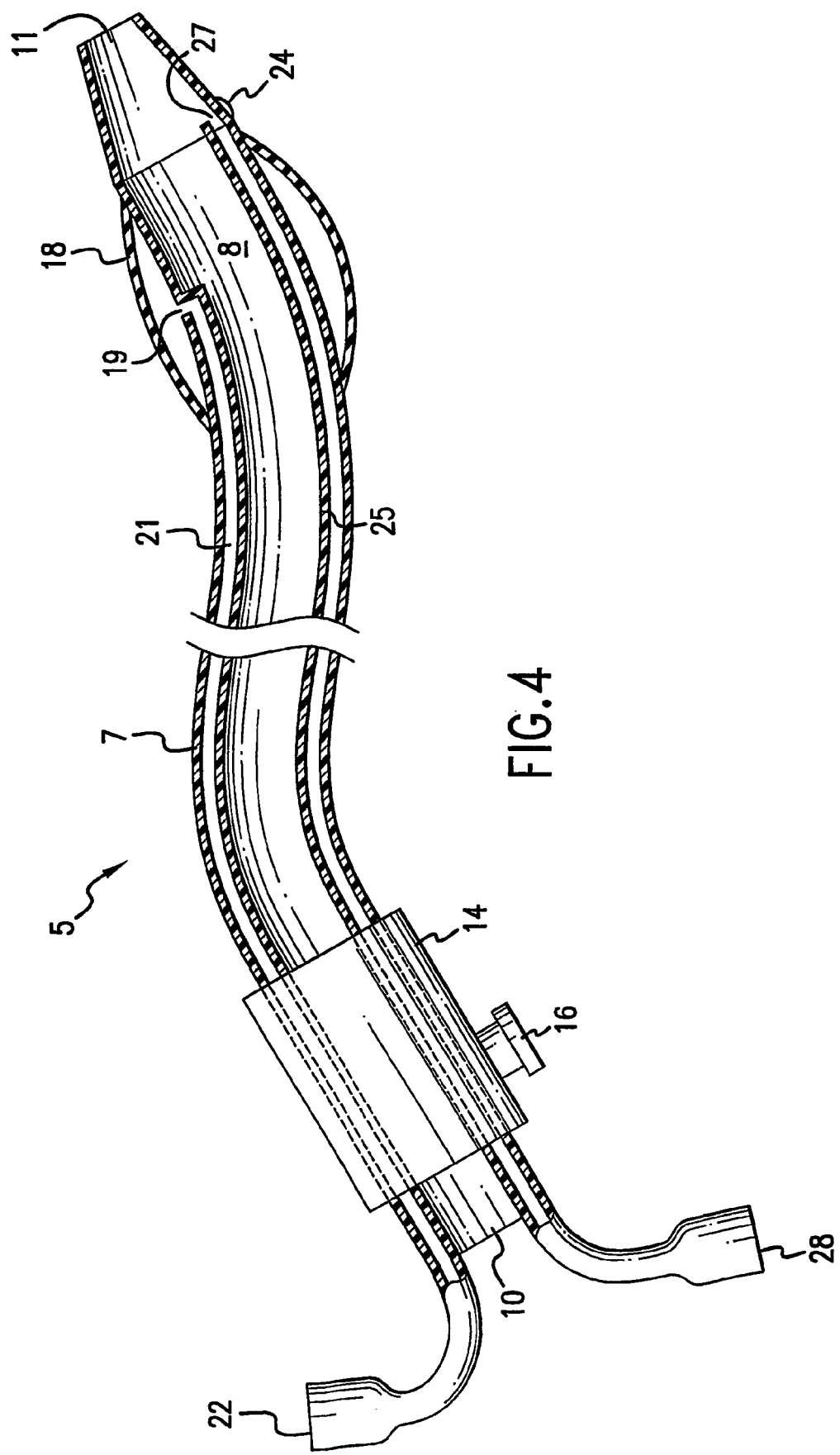
FIG. 4 is cross-sectioned view of a second embodiment of the catheter of the invention having a drug delivery lumen formed therein.

As shown in FIGS. 1 and 4, a solid state pressure sensor 24 may be affixed to the exterior of, or otherwise formed, positioned, or embedded within the distal end of the catheter body, and is adapted for use in measuring the target or ambient fluid pressure(s) at the distal or treatment end of the catheter during catheterization, as well as during the infusion of any fluids through the distal end of the catheter and into the arteries, veins, organs, or tissues of the patient. The distal pressure sensor may thus comprise any one of the known types of solid-state transducers for sensing and transmitting high fidelity pressure signals such as those manufactured by Millar Instruments, Inc. of Houston, Tex., as well as any other type of solid state transducer which is adapted for use in pressure or tactile sensation measurement. The lead wires of the sensor 24 are passed to a suitable plug (not illustrated) positioned at the proximal end of the catheter, and may therefore be passed through a communications channel 49 (FIG. 8) defined within the body of the catheter, or through an existing passageway, for example the passageway 31 (FIGS. 2 and 6) of the fluid-filled pressure sensor available for use with the catheter of this invention.

Figure 6:
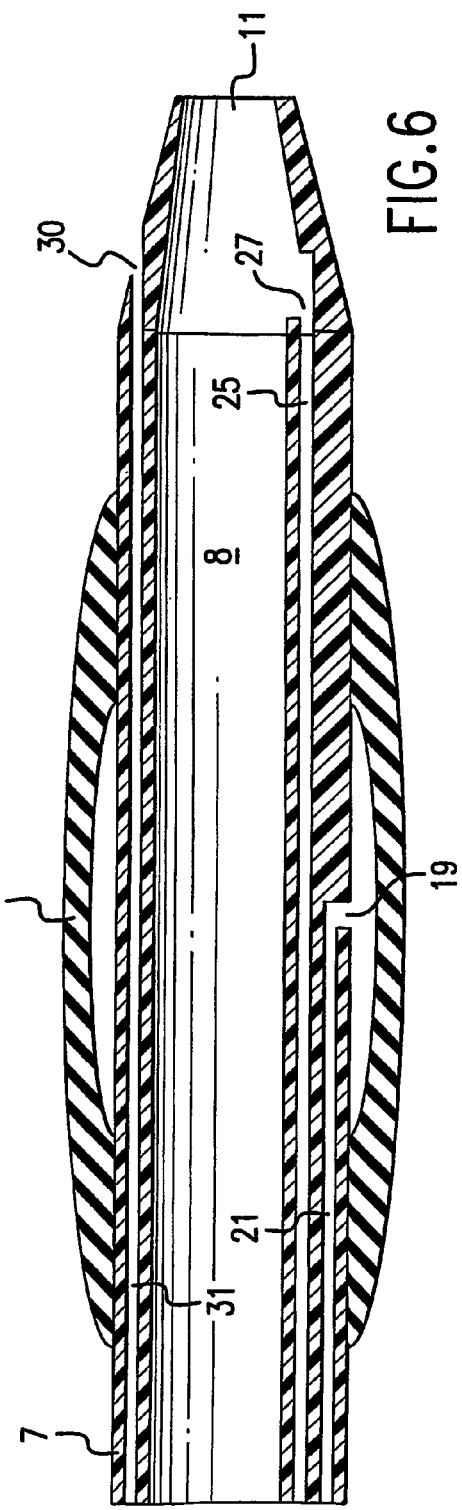
FIG. 6 is a cross-sectioned view of the distal end of the catheter of FIG. 4.

Referring now to FIGS. 2 and 6, an alternate embodiment of the catheter is disclosed having an alternate means for measuring the pressure at the distal end of the catheter. As shown in these two figures, the distal end of the catheter is provided with a fluid-filled distal pressure port 30 defined therein and extending in sealed fluid (hydraulic) communication through a passageway 31, defined within the catheter, to a suitable discharge port (not illustrated), for example a luer type of port, to which a suitable fluid pressure measurement device, for example one of the known types of fluid-filled transducers, is connected. The use of fluid filled passageways, and of fluid-filled pressure ports for measuring fluid pressures is well known and within the scope of those skilled in the art, and thus is not described in greater detail herein.

Referring now to FIGS. 4 and 6, yet another embodiment of the catheter of this invention is disclosed. In this embodiment of the catheter a distal drug outlet or delivery port 27 is defined within an elongate drug delivery lumen 25 defined within and extending in the lengthwise direction of the catheter body. The drug delivery lumen 25 is defined within the catheter body separately of the central lumen 8 thereof such that the fluids passed therethrough will not mix with those within the central lumen, but will instead be mixed at the distal tip of the catheter. The drug delivery port is formed to be in sealed fluid-tight communication with the drug delivery lumen. The drug delivery lumen also has a drug infusion port 28 defined therein, as illustrated in FIG. 4, for the passage of drugs or drug-fluid admixtures therethrough and into the drug delivery lumen.

So provided, the drug delivery lumen allows for the delivery of fast-acting, and/or rapidly degrading drugs through the distal end of the catheter, and into the treatment area within the surrounding arteries, veins, organs, or tissues of the patient. Examples of fast-acting and/or rapidly degrading drugs of the type that may be used with the invention include, but are not limited to, adenosine and nitric oxide. The distal infusion of these drugs through the drug lumen will prevent these short-acting agents from being metabolized or otherwise degraded by blood or other fluids during transit in the catheter lumen, and/or will prevent the interaction of the drugs before they enter the patient's blood stream, organs, or tissues.

In use, the catheter is introduced into the appropriate arterial or venous vasculature and guided to the target area through a pre-placed sheath-and guidewire, and guided to the target location in known fashion. In a first method of use therefore, the catheter may be fluoroscopically guided into a coronary artery that is partially or entirely blocked. The catheter is positioned at the point of occlusion, and the occlusive balloon is inflated as it is used in an angioplasty procedure, for example. In one embodiment of the procedure, the balloon can then be deflated and a cardioprotective agent may be infused at the physician's discretion to attenuate reperfusion injury or arrhythmias, or to introduce a local anti-arrhythmic or local inotropic agent.

In an alternate method of use, the catheter can be placed across the blockage and then inflated as per the use of an angioplasty catheter, and left deployed to introduce blood, fluids, or blood-fluid mixtures therethrough while preventing the admixture of native blood and blood flow therewith. The blood or blood-fluid mixture may contain cardioprotective drugs or anti-arrhythmic drugs to once again attenuate reperfusion injury, and so on. If so desired, blood or blood-fluid mixtures (i.e., hemodiluted blood) can be introduced through the catheter to prevent ischemia during the period of occlusive balloon inflation. As known, the benefit of including blood in a blood-fluid mixture is that oxygen is provided to the tissue, nutrients and endogenous substrates are included, as are endogenous anti-oxidants. Also, the flow rate and the pressure of the fluid can be controlled to stay within physiological and target therapeutic limits.

The complete occlusion of the blood vessel allows the physician to control the composition of the perfusion fluid, its flow rate, and pressure to the distal tissue or organ. In another embodiment of the procedure, the balloon may be partially deflated, or deflated according to a specified time algorithrim proceeding from full inflation to full deflation to allow for controlled blood flows. In addition, the time duration of inflation can be controlled by appropriate and known types of balloon inflation-deflation devices connected to the proximal end of the catheter at the luer lock (or other configuration) port.

By providing the drug delivery lumen 25, in association with the drug delivery port 27, rapidly deactivated drugs may be passed therethrough which allows for the admixture of drugs at the tip, i.e., the distal end, of the catheter rather than in the proximal portion thereof, or in the delivery device (not illustrated) affixed to the fluid-tight connector at the proximal end of the catheter. The desired drug or drugs will be infused through the drug infusion port 28 at the proximal end of the catheter, and outside of the patient's body.

Figure 8:
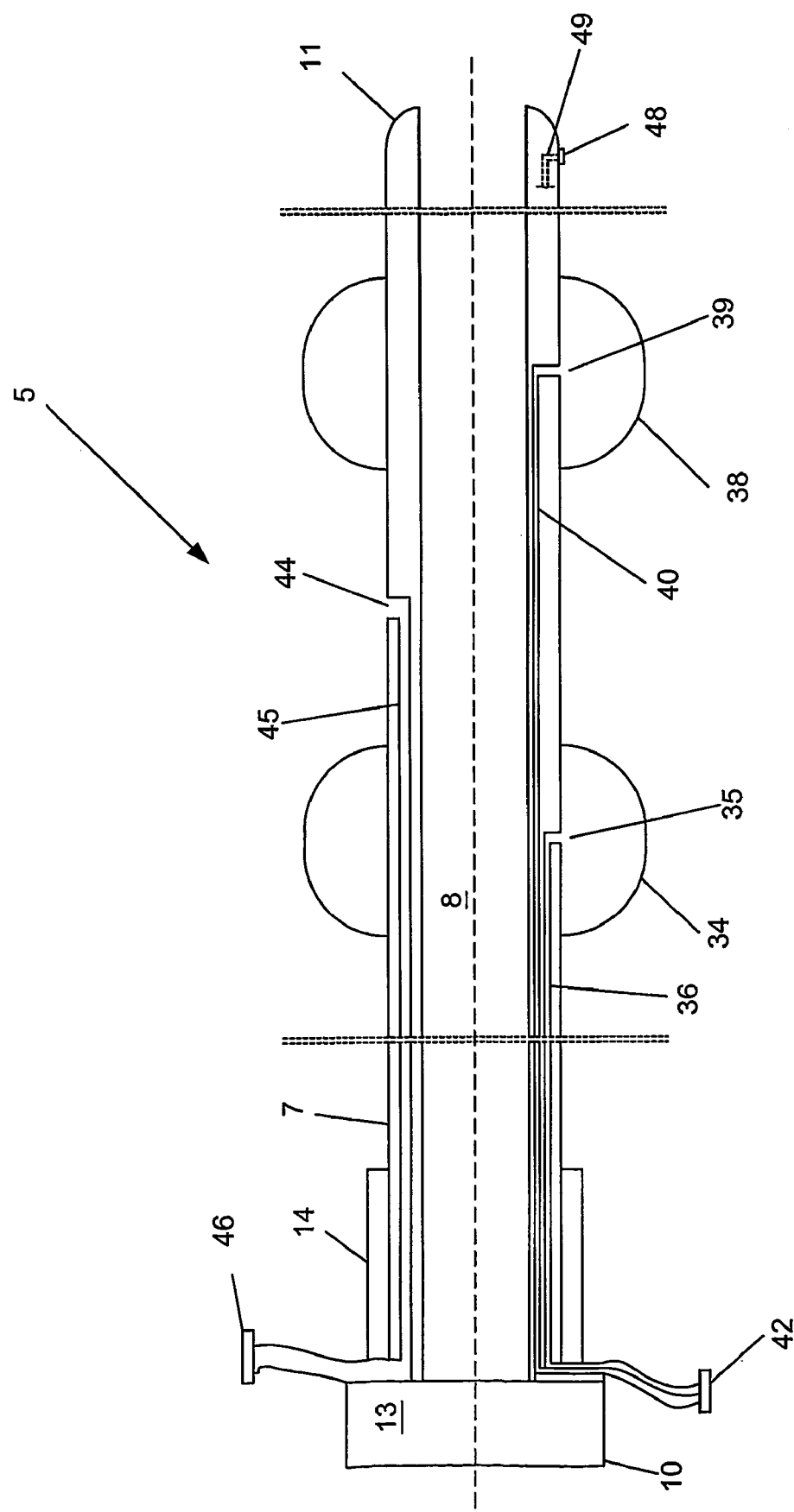
FIG. 8 is a cross sectioned view of a two occlusive balloon embodiment of the catheter of the invention.

Referring now to FIG. 8, a double balloon, or two balloon, embodiment of the catheter is illustrated. In this configuration a second occlusive balloon is spaced from the first occlusive balloon by a distance in the range of from approximately 0.5 to approximately 10 centimeters. This construction allows for the accumulation of fluids within this "inter-balloon" space. So constructed, this embodiment of the catheter allows for the measured delivery of medications into a target vessel wall by exposing the wall directly to the medications such that the inter-balloon space is used for accumulating the fluids and/or medications passed therein and that will, for example, bathe the vascular wall, the endothelium, or the plaque-containing area of the vessel wall.

The fluids/medications passed into the balloon inter-space can be retained in this space for a specified time, therefore allowing higher concentrations of the desired medications to be used than would otherwise be tolerated if given systemically. Thereafter, the medications/fluids can be re-aspirated into the catheter so that they are not delivered to the body, or can simply be washed into the general circulation when the balloons are deflated. The procedure for elimination of the medications used in the space between the balloons depends on toxicity and side effects of the medications. Applications using this construction of the balloon catheter include, but are not limited to, treatment for restenosis, localized endothelial injury, the stabilization of a plaque/plaque rupture, local coagulation, stabilization of the vascular endothelium by preventing inflammatory activation, attenuating cell proliferation by contact with anti-proliferative agents, delivery of gene therapy directly to the vessel wall, or other localized changes in the vessel wall or its constituents. In another application of this double balloon device, the space between the two balloons (the balloon inter-space) can be placed at the branch-point of a vessel, so that the fluid or drugs infused into this space, confined by the two balloons, will be selectively distributed into that branch.

Referring to FIG. 8, therefore, the catheter 5 is once again shown as having the elongate tubular body 7 with the continuous central lumen 8 defined therein extending from the proximal end 10 of the catheter body to the distal end 11 thereof. The catheter of FIG. 8 has a first occlusive balloon 34 positioned on the catheter body intermediate the proximal and distal ends thereof. An inflation port 35 is defined within the catheter body in fluid communication with a passageway 36 defined within the catheter body, and which extends to the proximal end thereof. A second occlusive balloon 38 is also positioned on the catheter body, intermediate the first balloon 34 and the distal end of the catheter. A second balloon inflation port 39 is defined within the tubular body of the catheter in fluid communication with a passageway 40 defined within the catheter body and extending to the proximal end thereof.

Each of the passageways 36, 40 are formed separately of one another, and each is also constructed to be placed into sealed fluid communication with a balloon inlet port or lumen 42 constructed to inflate the balloons 34,38, respectively, separately or together, as desired. An inflation syringe or bulb (not illustrated) will be attached to the inflation lumen 42 for inflating the occlusive balloons, and is constructed to allow for the inflation and/or deflation of the balloons separately or together, as desired, the syringe being of known construction and used in known fashion.

A drug delivery port 44 is defined within the catheter body such that it is positioned between the occlusive balloons 34 and 38, in what has been referred to as the balloon inter-space. The drug delivery port is in sealed fluid communication with a passageway 45 defined within the catheter body, which passageway extends in sealed fluid communication to a drug infusion port 46 at the proximal end of the catheter. The desired fluids, for example blood or blood-fluid mixtures, or drug admixtures, are therefore mixed externally of the catheter and are then passed into the drug infusion port, through the passageway 45, and exit the catheter body from the drug delivery port once at least one, or both, of the occlusive balloons have been inflated, as described in greater detail below.

Still referring to FIG. 8, the catheter is shown with a distal pressure sensor 48, which pressure sensor may be a solid-state sensor or a fluid-filled pressure port of the types described in greater detail above. The fluid-filled or solid-state pressure sensors are optional embodiments of the catheter. A conduit/passageway 49 is defined within the catheter body and extends from the pressure sensor to the proximal end of the catheter for connection to a suitable pressure measurement device of known construction for the type of pressure sensor being used. If, for example, a solid-state pressure sensor is used, the lead wires (not illustrated) which would extend from the sensor will be passed through the conduit 49 to the proximal end of the catheter body. Alternately, and if so desired, the lead wires from the solid-state pressure sensor may instead be embedded within the wall of the catheter body rather than passed through the conduit/passageway 49. If the pressure sensor is a fluid-filled port, however, then the passageway 49 will also be fluid-filled and will extend to a suitable fluid pressure measurement device (not illustrated), as known.

The method of using the two-balloon catheter of FIG. 8 includes the steps of inserting the catheter into the desired artery, vein, vessel or conduit within the body for treating a segment of the conduit by isolating the target segment through the inflation of the two occlusive balloons. Once the balloons are inflated, the desired blood, fluids, and/or medications are injected into the catheter and passed through the drug delivery port into the inter-space between the balloons to "dwell" in this area. As the volume of this area is known, a corresponding and pre-determined volume of the desired fluids/drugs can be injected into the inter-balloon area to prevent the spillover and possible distribution of the fluids/drugs into the patient or system beyond this defined area. Thereafter, the medications may be evacuated from the inter-space back through the drug delivery port in order to avoid any toxicity, or the medications may be allowed to wash out into the system by deflating the balloons if appropriate. This construction is useful where the catheter diameter may not support the flow of blood therethrough, i.e., the catheter is a low-profile configuration, and may also allow for the delivery of blood, fluids, and/or combinations therethrough to metabolically support the distal tissue and prevent ischemia therein, or provide for the delivery of tissue-protective medications.

It is anticipated that either or both of the pressure sensor arrangements described herein may be used with any one of the several embodiments of the catheter of the invention described herein, as desired. It is also anticipated that the catheter of the invention may be used with or without a drug delivery lumen formed as a part thereof, if so desired. Accordingly, it is anticipated that the catheter of this invention may be used with any desired one or combination of a distal pressure sensor and/or a drug delivery lumen as disclosed hereinabove, as well as with one or two occlusive balloons, as described in greater detail below. Therefore, the catheter of the invention may include any one or combination of the several features disclosed hereinabove in a single catheter, as desired.

The catheter 5, in all of its embodiments as illustrated in FIGS. 1-8 hereof, is constructed of known materials, which materials are particularly suited for, and approved for use in surgical or intravascular procedures. The central lumen 8 of the catheter is sized sufficiently for the delivery of fluids, blood, or blood-fluid mixtures therethrough. The occlusive balloons 18, 34, and 38, respectively, are each sized and shaped so that they may be inflated through their respective balloon inflation ports 19, 35, and 39 such that the respective balloons seal the artery or vein within which they are received, and to also allow for the infusion of the desired blood, or blood-fluid mixtures in a controlled manner through the catheter and into the veins, arteries, conduits, or tissues without the admixture of blood in the proximal portion of the catheter. The respective balloons can also be partially inflated to allow for a mixture of the blood from the patient's vessel with any crystalloid or drugs passed through the central lumen and/or the drug delivery lumen.

Each of the distal pressure sensors 24 and 49, as well as the distal pressure port 30, can be used to measure the distal fluid pressures in the vessel or organ during catheterization or infusion of the blood, fluid, or blood-fluid mixtures into the patient, and can also be used to control the flow rate of fluid therethrough if, for example, a separate infusion pump or device (not illustrated) is being used. In the alternative, the distal pressure sensor may be used to measure the distal fluid pressures for the determination and the calculation of the coronary or other vascular reserves thereat, or other vascular indices in which pressure is used as a coefficient.

Although several embodiments of the invention have been disclosed in the foregoing specification, it is understood by those skilled in the art that many modifications and other embodiments in the invention will come to mind to which the invention pertains, having the benefit of the teaching presented in the foregoing description and the associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention, and the words "a," "and," or "the" as they appear hereinabove may mean one or more, depending upon the context in which the words are used.

I claim:

1. A catheter adapted for use in passing fluids therethrough and into the arteries, veins, tissues, conduits, or organs of a patient, said catheter comprising:
   an elongate tubular body having a proximal end and a spaced distal end;
   a central lumen defined within said body and extending from the proximal end to the distal end thereof;
   means approximate the proximal end of said body for sensing a systemic fluid pressure therein the patient, comprising a sheath extended about an exterior periphery of said body and positioned approximate the proximal end of said body;
   means positioned at the distal end of said body for sensing the fluid pressure thereat;
   means for selectively adjusting the flow rate of fluid supplied to the central lumen based at least in part on the sensed systemic fluid pressure and the sensed fluid pressure at the distal end of the body;
   a first occlusive balloon disposed on the exterior of said body; and
   means for inflating said first occlusive balloon.

2. The catheter of claim 1, further comprising a drug delivery lumen defined within said body separately of said central lumen and extending in the lengthwise direction of said body, a drug delivery outlet at the distal end of the body in fluid communication with the drug delivery lumen, and a drug infusion port in fluid communication with the drug delivery lumen.

3. The catheter of claim 1, wherein said sheath defines an outlet port therein.

4. The catheter of claim 3, further comprising a pressure measurement device in sealed fluid communication with said outlet port.

5. The catheter of claim 3, wherein the pressure outlet port further comprises a luer-type of connector.

6. The catheter of claim 3, further comprising a fluid-filled transducer in sealed fluid communication with the pressure outlet port.

7. The catheter of claim 1, said means for sensing the fluid pressure at the distal end of the catheter comprising a solid-state pressure measurement device.

8. The catheter of claim 7, wherein said solid-state pressure measurement device is embedded within the tubular body of the catheter.

9. The catheter of claim 7, said solid-state pressure measurement device comprising a transducer.

10. The catheter of claim 1, said means for sensing the fluid pressure at the distal end of the catheter comprising a fluid-filled pressure port.

11. The catheter of claim 1, said means for inflating the first occlusive balloon comprising an elongate balloon inflation passageway defined within the tubular body, a balloon inflation port defined with the tubular body in fluid communication with said passageway and the interior of said first occlusive balloon, and a balloon inlet port in fluid communication with said passageway.

12. The catheter of claim 1, further comprising a luer-type of connector disposed at the proximal end thereof and in sealed fluid communication with the central lumen.

13. The catheter of claim 1, further comprising a second occlusive balloon spaced from the first occlusive balloon.

14. The catheter of claim 13, said second occlusive balloon being spaced from the first occlusive balloon by a distance in the range of from approximately 0.5 to approximately 10 centimeters.

15. The catheter of claim 1, wherein the sensed fluid pressure at the distal end of the body is substantially equal to the sensed systemic pressure after the flow rate of fluid is selectively adjusted.

* * * * *